US010765823B2

United States Patent
Laksov (10) Patent No.: US 10,765,823 B2
(45) Date of Patent: Sep. 8, 2020

(54) CONTROL DEVICE FOR MEDICAL VENTILATORS

(71) Applicant: Mindray Medical Sweden AB, Sundbyberg (SE)

(72) Inventor: Joakim Laksov, Danderyd (SE)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 994 days.

(21) Appl. No.: 14/823,902

(22) Filed: Aug. 11, 2015

(65) Prior Publication Data

US 2016/0184541 A1 Jun. 30, 2016

(30) Foreign Application Priority Data

Aug. 11, 2014 (EP) ..................................... 14180452

(51) Int. Cl.
*A61M 16/00* (2006.01)
*G16H 40/63* (2018.01)

(52) U.S. Cl.
CPC .... *A61M 16/0069* (2014.02); *A61M 16/0051* (2013.01); *A61M 16/024* (2017.08); *G16H 40/63* (2018.01); *A61M 2205/3334* (2013.01); *A61M 2205/502* (2013.01); *A61M 2205/505* (2013.01); *A61M 2205/52* (2013.01)

(58) Field of Classification Search
CPC . A61M 16/0069; A61M 16/024; G06F 19/00; G16H 40/63
See application file for complete search history.

(56) References Cited

U.S. PATENT DOCUMENTS

| 5,801,699 | A | * | 9/1998 | Hocker | G06F 3/04817 715/837 |
| 2007/0227537 | A1 | * | 10/2007 | Bemister | A61M 16/021 128/200.24 |
| 2008/0000479 | A1 | * | 1/2008 | Elaz | A61B 5/412 128/204.23 |
| 2009/0107498 | A1 | * | 4/2009 | Plattner | A61M 16/024 128/204.23 |

(Continued)

FOREIGN PATENT DOCUMENTS

| WO | 9720592 A1 | 6/1997 |
| WO | 2011063384 A1 | 5/2011 |
| WO | 2014005106 A1 | 1/2014 |

OTHER PUBLICATIONS

Watkinson, John, 1994, Focal Pr; Ex-lib, pp. 2-3.*

*Primary Examiner* — Timothy A Stanis
*Assistant Examiner* — Cana A Gallegos
(74) *Attorney, Agent, or Firm* — Kory D. Christensen (57) ABSTRACT

Aspects of the subject technology relate to a control device for a medical ventilator. The control device has a user definable medical ventilator protocol and is configured to select a plurality of objects from a group of objects, wherein each of the objects are segments of the ventilator protocol, and each of the objects has at least one attribute. Further, the control device is configured to arrange the plurality of objects in a sequence, initiate the at least one attribute to define a property for each object in the plurality of objects, and execute the sequence. The medical control device gives the user flexibility to define and implement a medical ventilator protocol in a faster way than possible today and for different patients and/or ventilator situations.

17 Claims, 5 Drawing Sheets

(56) References Cited

U.S. PATENT DOCUMENTS

2013/0104891 A1* 5/2013 Steinhauer ........ A61M 16/0051
  128/204.18
2013/0199533 A1* 8/2013 Steinhauer ........ A61M 16/0057
  128/204.23

* cited by examiner

CONTROL DEVICE FOR MEDICAL VENTILATORS

BACKGROUND OF THE INVENTION

Field of the Invention

This disclosure pertains in general to the field of medical control devices for defining a medical ventilator protocol.

Description of the Prior Art

It is well known that medical ventilators of today are reliable machines that have high requirements on its use and operation due to their critical interaction with a patient. The operation of the ventilator during use with the patient connected to it is secured by a protocol established by the ventilator manufacture. Each protocol is an established and verified step-by-step implementation on how the ventilator should function when running specific ventilator tasks in relation to the patient.

This means that once the manufacturer has decided on the protocol and the protocol is implemented in the ventilator it takes a lot of work for the manufacturer to change or add a new protocol to the ventilator. For example, if a medical doctor or doctors would want to try a new procedure or finds implications for a better procedure (protocol) to a certain situation, the manufacturer would like to have evidence that supports a change or an addition of a new protocol due to the burden for the manufacturer to implement the protocol in the medical ventilator. Such evidence is often acquired through a clinical trial which in turn takes a long time to complete. Thus, acquiring the evidence for the new procedure takes long time and after the trial it is still not certain that the ventilator manufacturer would like to change or add the protocol.

Another drawback with today's medical ventilators is that the protocols are most often not suitable for all patients. For example, there are many different ways of weaning and titrating and some of them are better suited for some patients than other patients. There are also some protocols which are better suited for some parts of the world than others due to physical differences of the patients and to get a global acceptance of a protocol that suits most people in the world thus takes a very long time.

A further drawback is that there are many protocols that require hospital personnel to be present and takes a long time to run, such as a PEEP titration. Such long run time protocols in combination with the very limited time that the hospital personnel have available to spend with the patient are contributing to increased stress for the hospital personnel and/or adds economic burden to the hospital when the need for more personnel to be hired is increased in order to maintain the patient safety at a ventilator department at the hospital.

Hence, an improved medical ventilator allowing for faster implementation of new protocols would be beneficial.

SUMMARY OF THE DISCLOSURE

Accordingly, examples of the disclosure preferably seek to mitigate, alleviate or eliminate one or more deficiencies, disadvantages or issues in the art, such as the above-identified, singly or in any combination by providing a device, a system, a method or a computer-readable medium according to the appended patent claims allowing for a user to define a medical ventilator protocol.

According to one aspect of the disclosure, a control device for a medical ventilator is disclosed. The control device has a user definable medical ventilator protocol and the control device includes means for selecting a plurality of objects from a group of objects, wherein each of the objects are segments of the ventilator protocol, and each of the objects have at least one attribute. Further, the control device includes means for arranging the plurality of objects in a sequence, means for initiating the at least one attribute to define a property for each object in the plurality of objects and a processor unit configured to execute the sequence. The medical control device gives the user flexibility to define and implement a medical ventilator protocol in a faster way than possible today and for different patients and/or ventilator situations.

According to another aspect of the disclosure, a system for a medical ventilator comprising the control device is provided. By having a system comprising the control device the user can define the medical ventilator protocol and use outputs and/or inputs in the system to affect and/or execute the protocol in relation to a patient.

According to yet another aspect of the disclosure, a method is provided for defining a medical ventilator protocol. The method includes selecting a plurality of objects from a group of objects, wherein each of the objects are segments of the ventilator protocol, and each of the objects have at least one attribute, arranging the plurality of objects in a sequence and initiating the at least one attribute to define a property for each object in the plurality of objects. By having a method for defining a medical ventilator protocol a user have the option to freely choose which medical ventilator steps that should be included in the medical ventilator protocol when defining the medical ventilator protocol.

According to a further aspect of the disclosure, a computer-readable medium having exemplified thereon a computer program for processing by a computer is provided. The computer program includes code segments for selecting a plurality of objects from a group of objects, wherein each of the objects are segments of the ventilator protocol, and each of the objects have at least one attribute, for arranging the plurality of objects in a sequence and for initiating the at least one attribute to define a property for each object in the plurality of objects. The use of a computer program to define the user definable medical ventilator protocol allows for a great flexibility for the user when defining the medical ventilator protocol due to the inherent flexibility of computer programs.

In one aspect of the disclosure, the plurality of objects allow for a protocol to be divided into smaller parts which can be individually selected by a user to suit the needs of the user and/or patient.

In another aspect of the disclosure, pre-defining the objects and basing them on existing protocols gives the user familiar starting objects from where to choose when defining the users own protocol.

In yet another aspect of the disclosure, pre-defining the objects and basing them on individual steps, actions, decisions present in existing protocols gives the user familiar starting objects from where to choose when defining the users own protocol.

In one aspect of the disclosure, by having the manufacturer defining the objects, the control device includes a database of common steps, actions or the like which the user can select from when defining its own protocol.

In another aspect of the disclosure, by having the option to adjust the attribute it is possible to construct advanced protocols of several objects where the attributes can be manually or automatically adjusted before or during the execution of the protocol.

Another aspect of the disclosure is by using static attributes the user needs to do the least of work when trying out a new protocol or if the user just wants to assemble a standard protocol as known and used at present.

Other aspect is, by allowing for the objects to be pre-selected, arranged in sequence and initiated it is possible for the user to select pre-defined protocols when in a hurry and/or when previously created by the user.

A further aspect is, by allowing for the objects to be read and/or written to a data storage medium it is possible to store the objects long term and/or temporary in the control device.

A further aspect is, by allowing for the objects to be read and/or written to the control device it is possible to share parts of a protocol, i.e. objects, with other users and/or update the control device with objects.

Yet a further aspect is, by allowing for the complete protocol to be read and/or written to the control device it is possible to share complete protocols with other users and/or update the control device with new complete protocols.

Some embodiments of the invention provide for a user to have a high degree of flexibility to adapt a user definable medical ventilator protocol for e.g. a specific patient, group of patients and/or a specific medical ventilator operation such as a procedure and/or a titration.

Some embodiments of the invention also provide for objects of a user definable medical ventilator protocol to have a pre-selected desired property aiding a user in the process of selecting objects suiting the user's needs and in an easy way completing the medical ventilator protocol.

Some embodiments of the invention also provide for creating and/or saving complete and/or parts of a protocol allowing for the protocols to be ready to be used instantly by the user.

Some embodiments of the invention also provide for future addition of objects not yet known or considered, i.e. future proofing a control device.

Some embodiments of the invention also provide for users to share and collaborate on protocols in a much easier and faster way than is possible today.

Some embodiments of the invention also provide for attributes to be changed and/or updated to be adapted for a patient and/or monitoring of physical parameters of the patient.

Some embodiments of the invention also provide for aiding a user by customizing means for selecting dependent on a task the user should perform.

Some embodiments of the invention also provide for aiding a user by customizing means for arranging dependent on a task the user should perform.

Further examples of the disclosure are defined in the dependent claims, wherein features for the second and subsequent aspects of the disclosure are as for the first aspect mutatis mutandis.

By use of the word static in this application it is meant that an object and/or an attribute are fixed from manipulation by an external source(s), a user(s) and/or other source during execution. For example, a time attribute defining the execution time of the protocol is set to a static attribute and to defined time interval, such as minutes, hours, days, weeks, months. Hence, when the defined time interval has been reached the protocol is ended. The use of static objects and/or attributes within control devices are well known to the skilled person and thus other static use may be applicable without diverting from the scope of the disclosure of this application.

By use of the word dynamic in this application it is meant that an object and/or an attribute may be altered by an external source(s), by a user(s) and/or other source during execution. For example, a pressure attribute defining the patient pressure is defined in the protocol, is set to a dynamic attribute and associated to a patient pressure sensor. The pressure attribute is updated and when the pressure attribute reaches a certain value the protocol is ended. The use of dynamic objects and/or attributes within control devices are well known to the skilled person and thus other dynamic use may be applicable without diverting from the scope of the disclosure of this application.

BRIEF DESCRIPTION OF THE DRAWINGS

These and other aspects, features and advantages of which examples of the disclosure are capable of will be apparent and elucidated from the following description of examples of the present disclosure, reference being made to the accompanying drawings, in which.

DESCRIPTION OF THE PREFERRED EXAMPLES

Specific examples of the disclosure will be described with reference to the accompanying drawings. This disclosure may, however, be exemplified in many different forms and should not be construed as limited to the examples set forth herein; rather, these examples are provided so that this disclosure will be thorough and complete, and will fully convey the scope of the disclosure to those skilled in the art. The terminology used in the detailed description of the examples illustrated in the accompanying drawings is not intended to be limiting of the disclosure. In the drawings, like numbers refer to like elements.

The following description focuses on an example of the present disclosure applicable to a control device and in particular to a control device for a user defined medical ventilator protocol.

Figure 1:
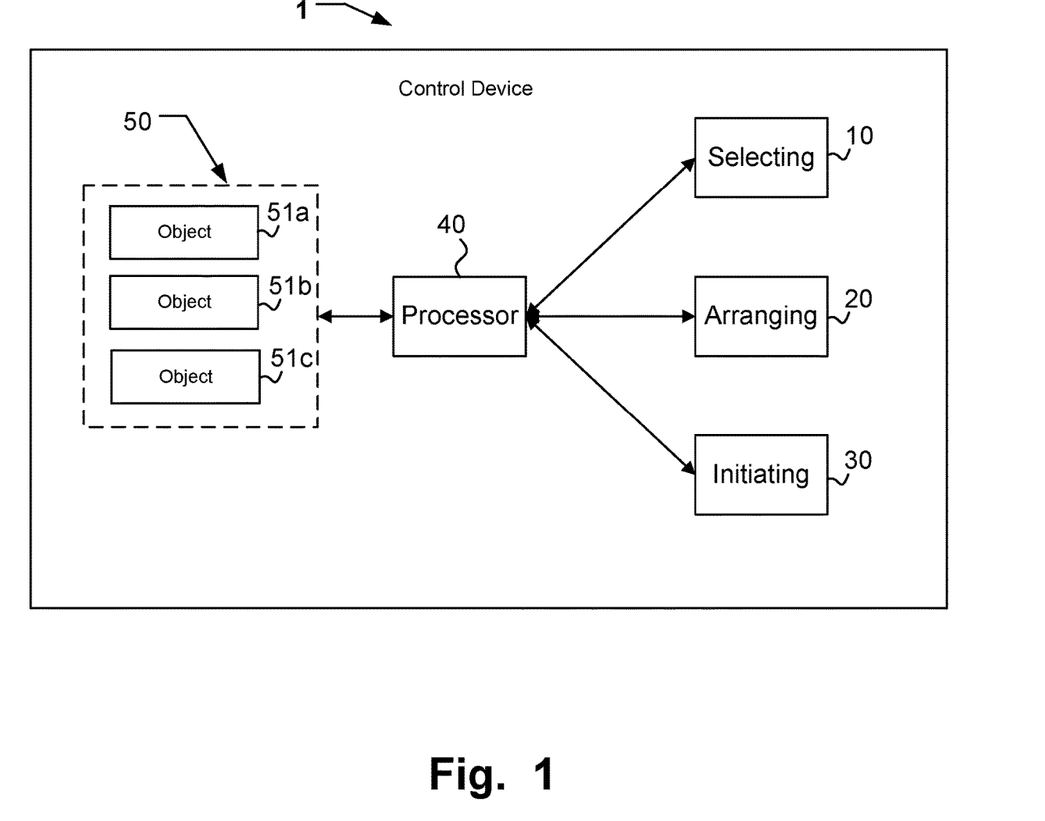
FIG. 1 illustrates a block diagram of an example of a control device for defining a medical ventilator protocol according to the disclosure.
Figure 2:
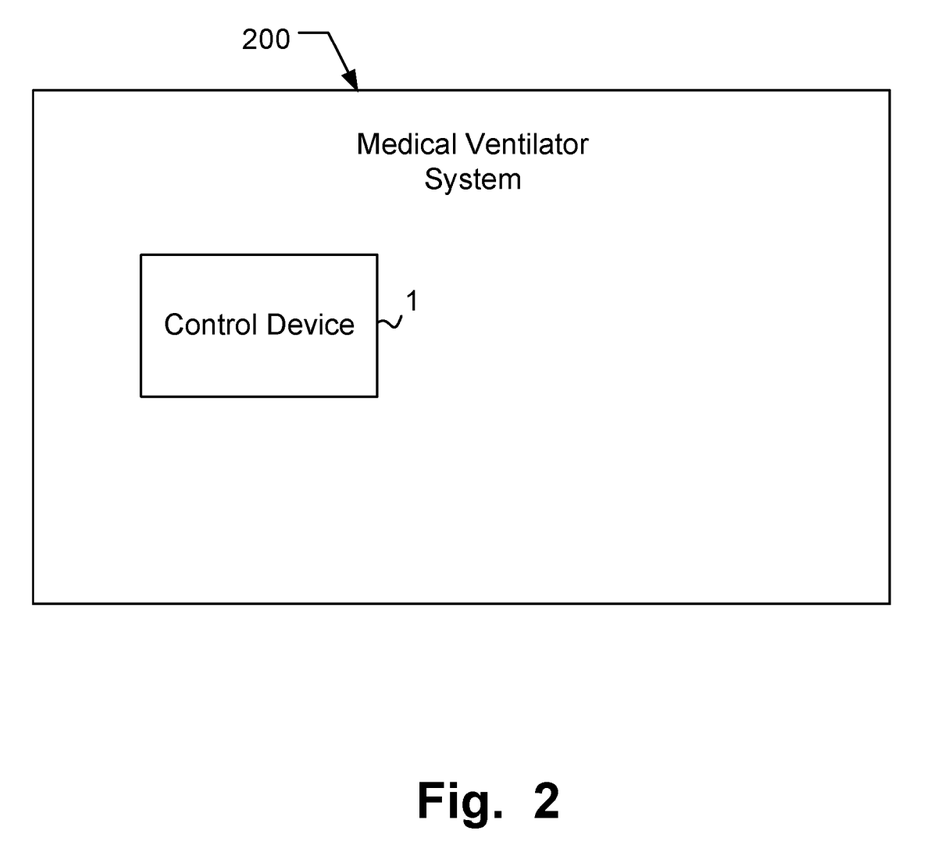
FIG. 2 illustrates a system comprising a control device for defining a medical ventilator protocol according to the disclosure.

FIG. 1 illustrates an example of (1.) a control device 1 for a medical ventilator, the control device 1 having a user definable medical ventilator protocol. The control device 1 includes means for selecting 10 a plurality of objects 51*a-c* from a group of objects 50, wherein each of the objects 51*a-c* are segments of the ventilator protocol, and each of the objects 51*a-c* have at least one attribute. The control device further includes means for arranging 20 the plurality of objects 51*a-c* in a sequence, means for initiating 30 the at least one attribute to define a property for each object 51*a-c* in the plurality of objects 51*a-c* and a processor unit 40 configured to execute the sequence. By having the control device 1 comprising means for selecting 10, arranging 20, initiating 30 the plurality of objects (segments) 51*a-c* and the processor unit 40 for executing the sequence of objects 51*a-c*, the user is given a high degree of flexibility to adapt the user definable medical ventilator protocol for e.g. a specific patient, group of patients and/or a specific medical ventilator operation such as a procedure and/or a titration. In one example seen in FIG. 2, the control device 1 is used in (15.) a medical ventilator system 200.

Each of the objects 51a-c is as described above a part (segment) of the medical ventilator protocol and each object 51a-c is given a desired property of the medical ventilator protocol by the selection of the at least one attribute. Hence, the combining of the plurality of objects 51a-c, wherein each object 51a-c has its own property based on the selection of the at least one attribute, defines the medical ventilator protocol.

Each of the objects 51a-c may (2.) include pre-selected attributes. The attributes for each of the objects 51a-c are, in some examples, pre-selected by e.g. a manufacturer of the control device 1.

Additionally and/or alternatively, in some examples the attributes for each of the objects 51a-c are pre-selected by a manufacturer of medical ventilators utilising the control device 1.

By pre-selecting the attributes and thus giving the object 51a-c a desired property the user is aided in the process of selecting objects suiting the user's needs and in an easy way completing the medical ventilator protocol.

In some examples, the (3.) pre-selected attributes of each object 51a-c is based on individual steps, actions, decisions or the like present in existing medical ventilator protocols. By having objects 51a-c being based on existing medical ventilator protocols, the user is presented with familiar segments from existing protocols e.g. widespread commonly used individual protocol steps, actions, decisions or the like which helps the user to more easily define the user definable medical ventilator protocol.

Additionally and/or alternatively, at least one object 51a-c may be added by the user and/or manufacturer which are not present in existing medical ventilator protocols. Such objects 51a-c, may be objects 51a-c that are useful for operating the medical ventilator, displaying a graphical user interface (GUI) and/or aiding the user, an object 51a-c for aiding the user when selecting other objects 51a-c, an object 51a-c for inputting data to other objects 51a-c at least one attribute and/or an object 51a-c for displaying information from other object(s) 51a-c. The object 51a-c may, for example, be (4.) a help text object, an attribute input object, an observation object, a titration object, a temporary attribute adjustment object, a comfort zone object, an undesired ventilation object, an action object, a decision object, an attribute adjustment object, an trend attribute display object, an attribute display object, a time of day object, a weaning object, an add on pressure support object, a logging block, a sound object, an alarm object and/or an easy access object.

Additionally and/or alternatively, the user may create a new object 51a-c or new objects 51a-c by e.g. combining objects 51a-c in the group of objects 50 and/or by adding new attributes not associated with any object 51a-c in the group of objects 50 by use of external sources such as the use of input signals and/or input data to the control device 1 and/or physiological parameters to further customize the medical ventilator protocol and/or allow for future addition of objects 51a-c not yet known or considered, i.e. future proofing the control device 1. The new objects 51a-c may in some examples be based on the most commonly used object 51a-c and/or commonly used for a specific patient.

An example of a help text object is that the help text object is an icon that tells the user how to perform a task and/or what protocol is used. Another example of the help text object is that it is a recommendation of what ventilation mode the hospital recommends for a certain patient group. Further examples of the help text object is that it used for educating personnel in the hospital about how to perform tasks, terminology used in the ventilator, how to set the alarms and other associated ventilator tasks. For example, help text objects is used as tutorials and/or help text objects is used in series allowing for users to be guided through a step by step procedure. In yet another example the user can configure a text block to pop up when a certain state in the ventilator is reached and it can explain the next step. Another example is that the help text object is an "alarm" informing the user of a certain state of the patient that the ventilator does not have a specific alarm for. Another example where the help text object is used is in combination with a sound object for signalling of a non-critical event combined with help for how to proceed and/or resolve the problem.

The control device 1 may, in some examples include (7.) pre-selected objects 51a-c from the group of objects 50, the objects 51a-c are arranged in sequence and the at least one attribute associated with each object 51a-c is initiated, allowing for the program on the processor 40 to instantly execute the sequence. By having the objects 51a-c pre-selected, arranged in sequence and the at least one attribute of each object 51a-c to be initiated it is possible to create and/or save complete protocols ready to be used instantly by the user. Also, this could help the user in choosing a suitable protocol for the patient. Further, this could help the user in an emergency situation where the user uses the complete protocol immediately to save time. In another example, the user uses the complete protocols to add an additional and/or alternative object 51a-c for e.g. customizing the protocol dependent on the situation and/or the patient's needs and/or patient comfort. The user may also remove an object 51a-c present in the complete protocol to customise the protocol.

The control device 1 may in some examples further include (8.) means for reading and/or writing the objects 51a-c to a data storage medium. By allowing for the objects 51a-c to be read and/or written to and/or from the control device 1 the control device 1 can be updated with new objects 51a-c and/or the objects 51a-c can be saved to the data storage medium for processing, long term storage and/or temporary storage. This also allows for users to share and/or collaborate on parts of protocols in a much easier and faster way than is possible today. In another example a computer is used to create and/or store the objects 51a-c. The objects 51a-c is then transferred to and/or from the computer to the control device 1.

The means for reading and/or writing may in some examples be adapted to (9.) read and/or write from/to the data storage medium the pre-selected plurality of objects 51a-c, which are arranged in sequence and each of the objects 51a-c have at least one initiated attribute. By adapting the means for reading and/or writing the pre-selected plurality of objects 51a-c, which are arranged in sequence and each of the objects 51a-c at least one attribute is initiated i.e. the complete protocol from/to the data storage medium, it is possible to transfer the complete protocol from one control device 1 to another control device 1. This allows for users to share and collaborate on protocols in a much easier and faster way than is possible today.

The data storage medium may in some examples be (10.) an internal data storage medium. In other examples an external data storage medium. Such internal data storage medium is e.g. a hard drive, RAM memory and/or the like commonly used internal data storage mediums. Such external data storage medium is e.g. a flash drive, a memory card or similar commonly known used external storage mediums.

In an example, each object 51a-c comprises (5.) at least one attribute initiated to be a dynamic attribute. By using a dynamic attribute it is possible for e.g. a user, an input signal and/or an input data to the control device 1, to change the attribute before the execution of the sequence. Additionally and/or alternatively, the dynamic attribute is changed during the execution of the sequence. This allows dynamic attributes to be changed and/or updated based on the patient and/or monitoring of physical parameters of the patient.

In yet another example, each object 51a-c comprises (6.) at least one attribute initiated to be a static attribute. By using a static attribute the user can set the attribute to a specific state which is maintained during the execution of the protocol and/or be presented with a pre-defined choice for the attribute aiding the user to in an easier and faster way complete the definition of the users own protocol. Such static attributes may be alarm levels, times, dates, pressure, other critical attributes and/or other attributes which not should be changed during the execution of the sequence.

In another example, each object 51a-c includes both at least one static and at least one dynamic attribute. By having the object 51a-c comprising static and dynamic attributes it is possible to e.g. compare the static attribute such as a value with the dynamic attribute such as a value updated based on e.g. sensor data, sensor signals and/or patient data. Alternatively in an example, the user defined protocol may include objects 51a-c only having static and/or dynamic attributes.

The at least one attribute associated with each object is in some examples a value, a character, a text, a data, a sound, a clinical parameter, a clinical setting, a clinical alarm, a technical alarm, a breathing mode and/or an image. Additionally and/or alternatively, in other examples the at least one attribute is (11.) a tidal volume (VT), an inspired VT, an expired VT, an breathing frequency, a total breathing count (ftot), a fspn, a fmand, an oxygen saturation (SpO2), an end-tidal carbon oxide (EtCO2), a positive end-expiratory pressure (PEEP), a PEEP start value, a PEEP end value, an oxygen concentration (FiO2), a minute ventilation (MV), a spontaneous minute volume (MVspont), a leakage minute volume (MVleak), a resistance, a compliance, a RSBI, a WOB, a NIF, a P0.1, an intrinsic PEEP (PEEPi), a body weight, a volume, a step size, a time, a duration, a number of repetitions, a maximum value, a minimum value, an alarm, a continuous positive airway pressure (CPAP), a patient chart, a diagram and/or a trend. Alternatively, the at least one attribute is another commonly known ventilator parameter.

In an example, the means for selecting 10, additionally and/or alternatively the means for arranging 20 the plurality of objects 51a-c comprises (12.) an input device, such as a keyboard, a touch screen, a computer mouse, a switch, a knob and/or a button. By having the control device 1 comprising a variety of means for selecting 10 and/or arranging 20 the objects 51a-c it is possible to e.g. customise the means 10, 20 dependent on the task the user should perform, in order to aid the user when defining the protocol. For example, the touch screen 10 is used to select the objects and the knob 10 is used for arranging the objects in sequence, aiding the user in not confusing the selections means 10 from the arranging means 20. Additionally in one example, the input device comprises a code segment.

Figure 3:
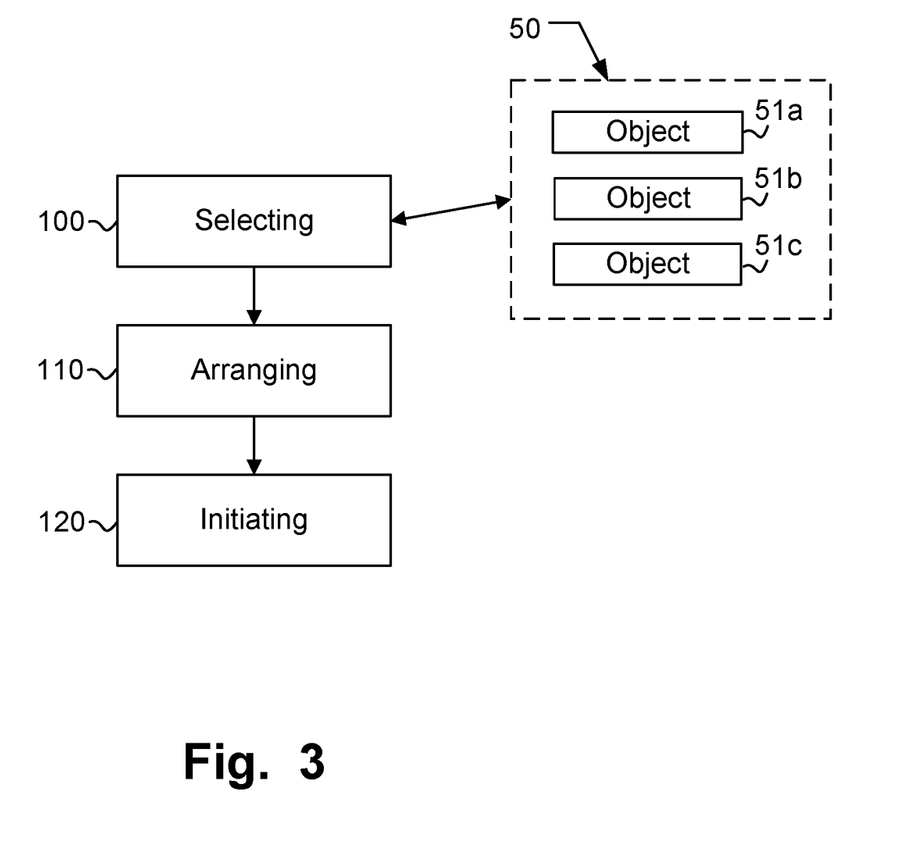
FIG. 3 is a flow chart of a method of using a control device for defining a medical ventilator protocol according to the disclosure.

A pre-treatment method for defining a medical ventilator protocol is exemplified below and seen in FIG. 3, wherein a (13.) selection 100 of a plurality of objects 51a-c from a group of objects 50, wherein each of the objects 51a-c are segments of the ventilator protocol, and each of the objects 51a-c have at least one attribute is performed.

Following, an arranging 110 the plurality of objects 51a-c in a sequence is carried out. In one example, the selection 100 of the first object 51a and arranging the first object 51a in the sequence is performed before the selection of a second object 51b and arranging the second object 51b in sequence is performed. In another example, the plurality of objects 51a-c is selected 100 before arranging 110 the plurality of objects 51a-c in sequence is carried out.

Following, an initiation 120 of the at least one attribute to define a property for each object 51a-c in the plurality of objects 50 is conducted. The initiation 120 of the at least one attribute is on example performed by a control device 1 to be a dynamic attribute. Alternatively and/or additionally, the control device 1 initiates the at least one attribute to be a static attribute. In yet another example, a user additionally and/or alternatively initiates 120 the attribute for the object 51a-c or each of the objects 51a-c.

Additionally, the pre-treatment method further comprises (14.) executing the sequence. The execution is in one example performed by a processor and in another example by a computer.

Following is an example disclosing a general use of the control device 1 for defining a user definable medical ventilator protocol. A medical ventilator system comprises the control device 1, a combined touch screen and monitor 10,20, a patient ventilator output and sensors. To define the desired ventilator protocol, a user clicks on the touch screen 10 to select a plurality of objects 51a-d from the group of objects 50. The user clicks on the observe object 51a and following the click, the user is shown a choice of using the static or the dynamic attribute of the observe object 51a.

The user selects the dynamic attribute and is prompted with the attribute input object 51e. The user inputs a start value for the observation object 51a. The dynamic attribute of the observation object 51a is linked too and will be continuously changed based on input data from the sensor(s). The user also selects the static attribute for the observation object 51a and is once again prompted with the attribute input object 51e. The static attribute is a time value defining a time for running the observation object 51a and in this case the time is chosen to 5 minutes.

Following, similar choices are made with respect to the decision 51b, adapt 51c and weaning objects 51d. The objects 51a-d are automatically arranged by the means for arranging 20 after the selection of the objects 51a-e in the order the objects 51a-d where chosen.

In the decision object 51b two attributes are initiated to be static, a minimum and maximum value. The values are compared to the dynamic attribute of the observation object 51a, i.e. too the continuously changing value based on the sensors data. Based on the comparison the decision object 51b triggers the adapt object 51c to perform an adaptation of the patient ventilator output. The adapt object 51c affects the patient ventilator output to improve the function of the lungs of the patient.

To end the user defined protocol the weaning object 51d is triggered by the time value of the observation object 51a.

When the user has completed the selection of objects 51a-d the user is prompted by the help text object 51f inquiring the user if the user is satisfied with the order in which the user selected the objects. If not, the user can re-arrange the order by use of the means of arranging 20 which in this example is the touch screen. When the user is satisfied with the sequence of the objects 51a-d, the user has created the user defined protocol and following, the processor 40 executes the sequence of objects 51a-d representing the user defined ventilator protocol.

As described above the sequence of the objects 51a-d should be executed as the objects 51a-d are arranged, but the objects 51a-d may use references and refer to each other and/or themself during the execution. By use of referring allows for loops to be introduced in the sequence. As described above the observation object 51a is first in the sequence, then the decision object 51b and then the adapt object 51c. Then the weaning object 51d should be next in the sequence but the adapt object 51c refers back to the observation object 51a, creating a loop that is run before the weaning object 51d is executed.

The above method uses triggers and/or referrals for/to other objects 51a-d in the sequence but the sequence could alternatively be sequenced with the actual number of objects 51a-d that are used in the above example and at their respective place creating the sequence representing the user defined medical ventilator protocol to be executed by the processor 40.

EXAMPLES

These examples are only for further illustrating the use of the disclosure according to the application and should not be considered as limiting to the scope of the disclosure according to the application.

Figure 4:
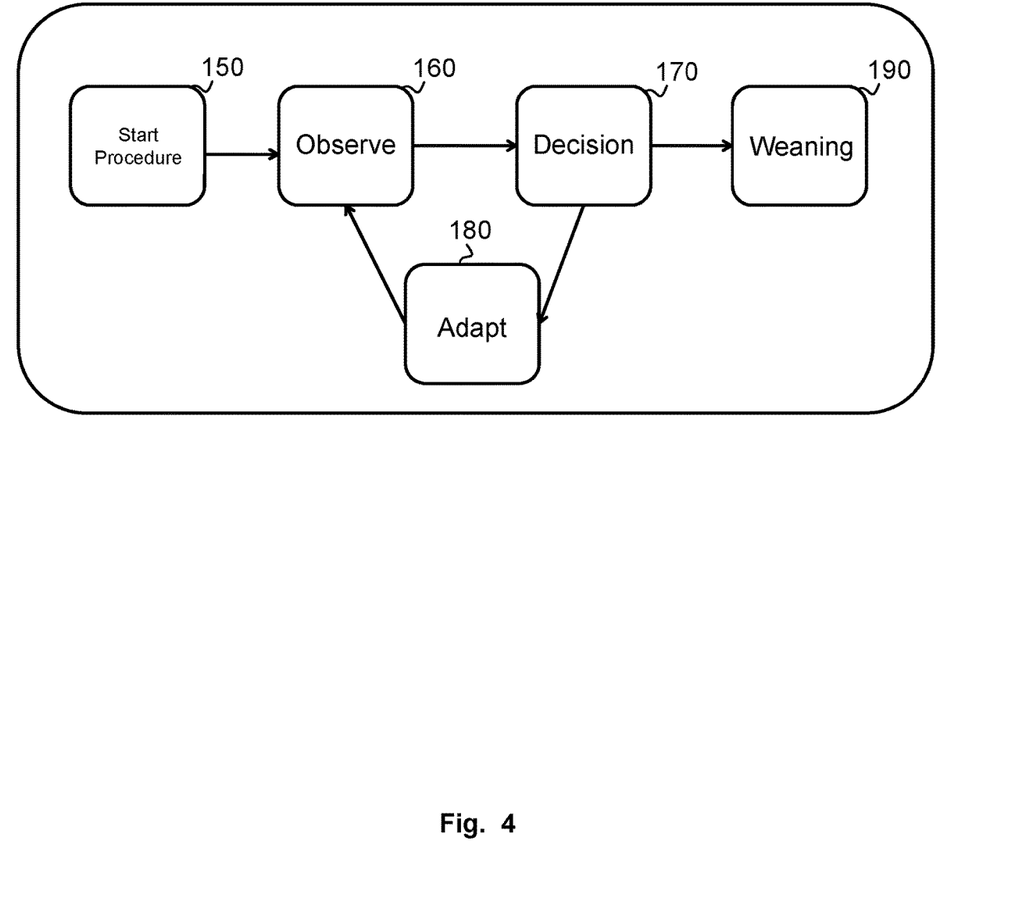
FIG. 4 is a flow chart of an exemplary method for weaning a patient.

In FIG. 4, an exemplary procedure is illustrated wherein the procedure starts 150 with observing 160 parameters of a patient for 1 minute. Following, a decision 170 is made based on the parameter values to wean or not, according to a weaning decision definition. If not, adapt 180 the settings according to a table and observe 160 once again. When the decision 170 is made to wean, based on the weaning definition, a weaning trial 190 is executed. The weaning trial 190 suggests extubation, perform manual or automatic weaning to the user.

Figure 5:
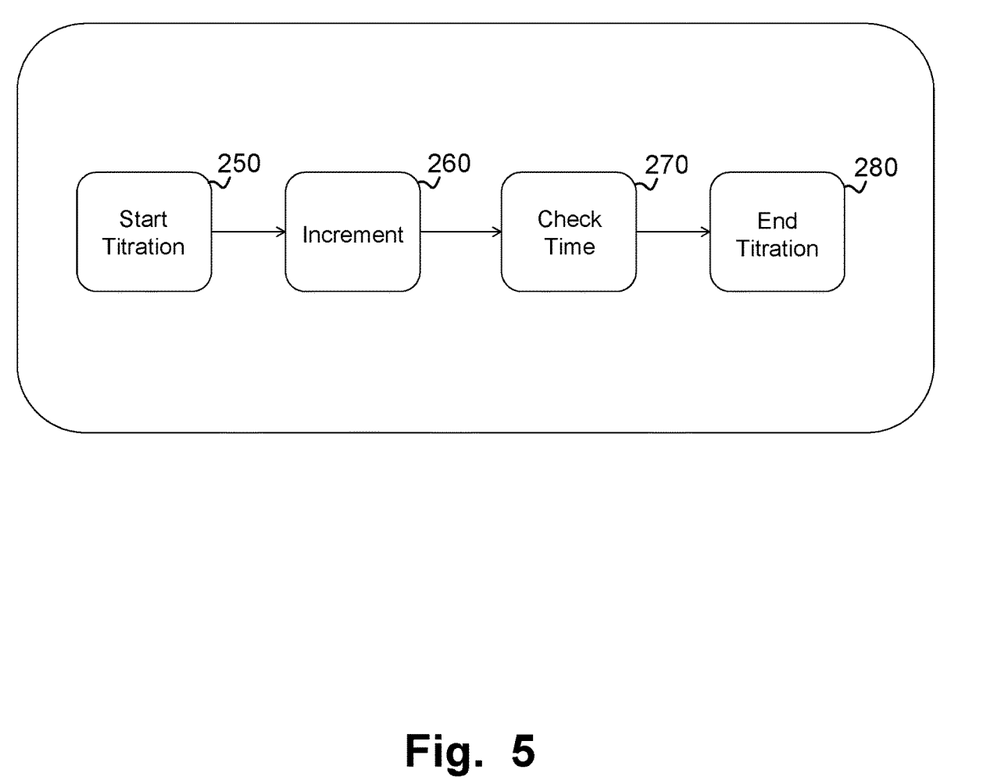
FIG. 5 is a flow chart of an exemplary method for titrating a value.

In FIG. 5, an example of a titration is illustrated. The titration starts 250 with incrementing 260 3 cmH2O from a start PEEP value of 10 cmH2O every fifth number of breaths until an end time of 3 minutes is checked 270. When the end time is reached the titration is ended 280.

In another example of a protocol, the control device 1 is controlled by an external input, such as from a patient's lung state. The control device 1 is configured to at least maintain or alternatively to improve the patient to a risk free state. What the risk free state is depends on e.g. the patient and/or hospital practice. In this example the external input comprises measurements of a tidal volume and that it lies within a specified range, a measurement of that the patient spontaneous breaths, a measurement of a specific breathing mode, a measurement of a oxygen concentration and that the oxygen concentration is below a certain value and that these measurement have been stable for a certain time period. When the condition of the stability is achieved, the patient is in the risk free state and can be removed from the support provided by the control device 1. A numerous of further protocols as the above based on measurements and/or actions is achievable by use of the disclosure of this application.

Another example of a protocol, the operator uses trends and/or statistics on a patient to monitor and/or control the patient's lungs by use of the control device 1. In another example the operator uses trends and/or statistics from at least two patients to control the patient's lungs by use of the control device 1. Values used for the trends and/or statistics is selected from a specified at least one patient related value and/or at least one measurement of the patient and/or values from an external measurement and/or operator inputted values. These values is in one example used for gathering information on which a specified at least one patient related value and/or at least one measurement of the patient and/or values from an external measurement and/or operator inputted values are most often used by the operator. Alternatively the objects 51a-c and/or parts of protocols and/or protocols are used to gather information on which procedures are most often performed by the operator.

As appreciated by the skilled person the present disclosure may be performed in numerous ways and the discloser in this application is mere examples of suitable ways of performing the disclosure. Further, it is also understood that the scope of the disclosure in this application extends beyond the examples given herein.

The present disclosure has been described above with reference to specific examples. However, other examples than the above described are equally possible within the scope of the disclosure. Different method steps than those described above, performing the method by hardware or software, may be provided within the scope of the disclosure. The different features and steps of the disclosure may be combined in other combinations than those described. The scope of the disclosure is only limited by the appended patent claims.

The invention claimed is:

1. A control device for a medical ventilator, the control device having a user definable medical ventilator protocol, wherein the control device includes:
   means for selecting a plurality of objects from a group of objects, at least one object of the plurality of objects comprising a wean object configured to wean a patient from the medical ventilator, wherein each of the objects are segments of the ventilator protocol, at least one of the objects having at least one static attribute and at least one dynamic attribute, wherein each static attribute maintains a particular value during the execution of the ventilator protocol, and wherein each dynamic attribute has a value that is updated during the ventilator protocol responsive to sensor data;
   means for arranging the plurality of objects in a sequence, wherein at least one object of the plurality of objects in the sequence refers to itself or another object to create a loop that must be performed before executing the wean object to wean the patient from the medical ventilator;
   a processor unit; and
   a non-transitory computer readable storage medium comprising instructions which, when executed by the processor unit, cause the processor unit to:
      initiate the at least one attribute to define a property for each object in the plurality of objects, and
      execute the sequence.

2. The control device according to claim 1, wherein each of the objects in the group of objects includes pre-selected attributes.

3. The control device according to claim 2, wherein the pre-selected attributes of each object is based on individual steps, actions, or decisions present in existing medical ventilator protocols.

4. The control device according to claim 1, wherein the plurality of objects further comprises at least one of a help text object, an attribute input object, a temporary setting adjustment object, a comfort zone object, an undesired ventilation object, an action object, a decision object, a setting adjustment object, a trend values display object, a values display object, a time of day object, an add on pressure support object, a logging block, a sound object, an alarm object, or an easy access object.

5. The control device according to claim 1, wherein the plurality of objects are pre-selected from the group of objects, the objects are arranged in sequence and the at least one attribute associated with each object is initiated, allowing for a program on the processor to instantly execute the sequence.

6. The control device according to claim 1, wherein the non-transitory computer readable storage medium further comprises instructions which, when executed by the processor unit, cause the processor unit to read and/or write the objects to a non-transitory data storage medium.

7. The control device according to claim 6, wherein the objects include a pre-selected plurality of objects, which are arranged in sequence and each of the objects has at least one initiated attribute.

8. The control device according to claim 6, wherein the non-transitory data storage medium is an internal data storage medium and/or the data storage medium is an external data storage medium.

9. The control device according claim 1, wherein the at least one attribute is a tidal volume (VT), an inspired VT, an expired VT, a breathing frequency, a total breathing count (ftot), a fspn, a fmand, an oxygen saturation (SpO2), an end-tidal carbon oxide (EtCO2), a positive end-expiratory pressure (PEEP), a PEEP start value, a PEEP end value, an oxygen concentration (FiO2), a minute ventilation (MV), a spontaneous minute volume (MVspont), a leakage minute volume (MVleak), a resistance, a compliance, a RSBI, a WOB, a NIF, a P0.1, an intrinsic PEEP (PEEPi), a body weight, a volume, a step size, a time, a duration, a number of repetitions, a maximum value, a minimum value, an alarm, a continuous positive airway pressure (CPAP), a patient chart, a diagram and/or a trend.

10. The control device according to claim 1, wherein the means for selecting and/or arranging includes a keyboard, a touch screen, a computer mouse, a switch, a knob and/or a button.

11. The control device according to claim 1, wherein each of the objects in the group of objects includes pre-selected attributes.

12. The control device of claim 1, wherein at least one static attribute of an object comprises a specified time period, and at least one dynamic attribute of the object comprises sensor data to be displayed for the specified time period.

13. The control device of claim 1, wherein at least one static attribute of an object comprises a specified alarm level, and wherein at least one dynamic attribute of the object comprises sensor data for comparison with the specified alarm level.

14. The control device of claim 1, wherein at least one object includes at least two static attributes specifying minimum and maximum values that are compared to at least one dynamic attribute.

15. A pre-treatment method for defining a medical ventilator protocol, the method comprising:

selecting a plurality of objects from a group of objects, at least one object of the plurality of objects comprising a wean object configured to wean a patient from the medical ventilator, wherein each of the objects are segments of the ventilator protocol at least one of the objects having at least one static attribute and at least one dynamic attribute, wherein each static attribute maintains a particular value during the execution of the ventilator protocol, and wherein each dynamic attribute has a value that is updated during the ventilator protocol responsive to sensor data;

combining a least two of the plurality of objects into a single new object that is selectable and arrangeable in a graphical user interface;

arranging the plurality of objects including the new object in a sequence, wherein at least one object of the plurality of objects in the sequence refers to itself or another object to create a loop that must be performed before executing the wean object to wean the patient from the medical ventilator;

initiating the at least one attribute to define a property for each object in the plurality of objects; and executing the sequence.

16. A medical ventilator system with a control device, comprising:

a processing unit;

a memory unit in communication with the processing unit;

a control sequence for execution by the processing unit comprising:

a selection segment for selecting a plurality of objects from a group of objects, at least one object of the plurality of objects comprising a wean object configured to wean a patient from the medical ventilator, wherein each of the objects are segments of a ventilator protocol, at least one of the objects having at least one static attribute and at least one dynamic attribute, wherein each static attribute maintains a particular value during the execution of the ventilator protocol, wherein each dynamic attribute has a value that is updated during the ventilator protocol responsive to sensor data, and wherein at least one dynamic attribute comprises a trend data including statistics obtained from a plurality of external measurements;

an arranging segment for arranging the plurality of objects in a sequence, wherein at least one object of the plurality of objects in the sequence refers to itself or another object to create a loop that must be performed before executing the wean object to wean the patient from the medical ventilator; and an initiating segment for initiating the at least one attribute to define a property for each object in the plurality of objects prior to executing the sequence by the processing unit.

17. The non-transitory computer readable storage medium of claim 16, wherein at least one object is a trend attribute display object configured to display the trend data including the plurality of external measurements.

* * * * *